Figure 1:
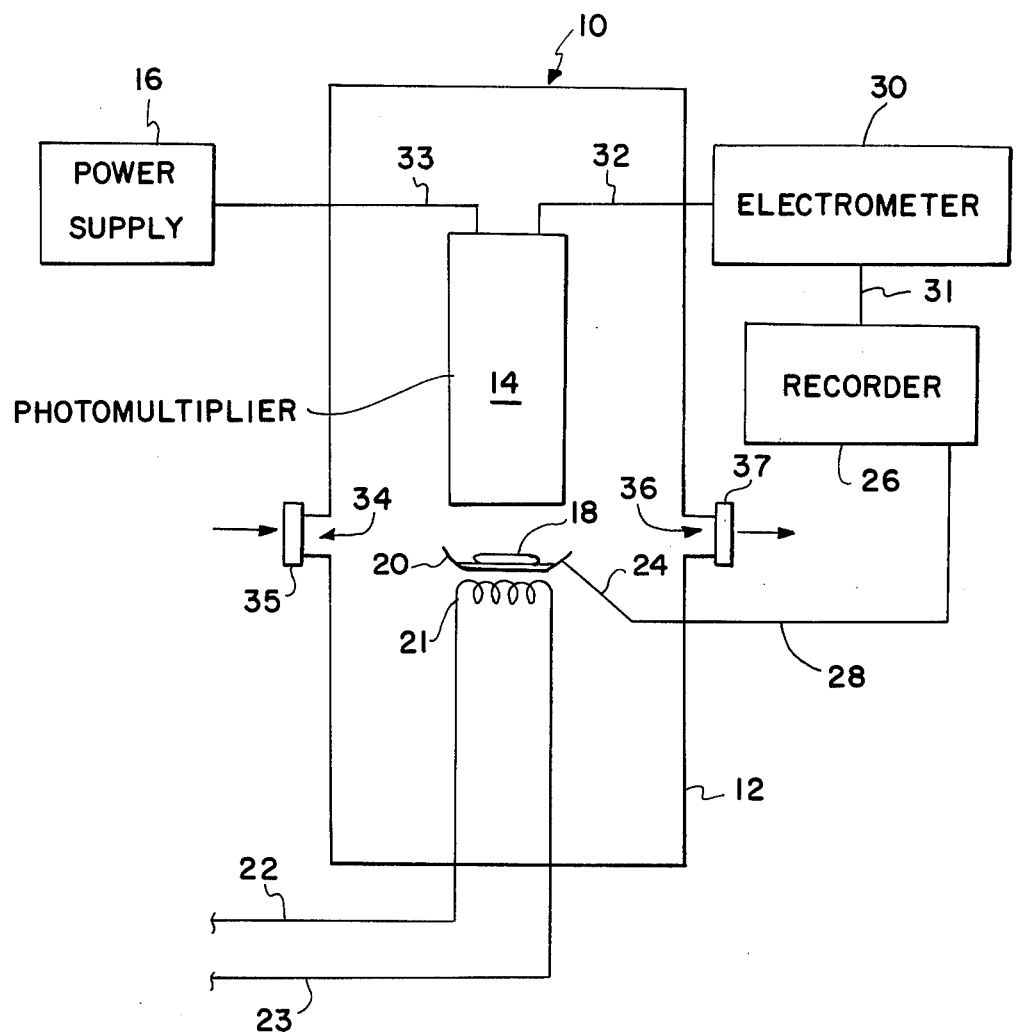

United States Patent [19]

Rogowski et al.

[11] 4,062,650

[45] Dec. 13, 1977

[54] THERMOLUMINESCENT AEROSOL ANALYSIS

[75] Inventors: Robert S. Rogowski; Edward R. Long, Jr., both of Hampton, Va.

[73] Assignee: The United States of America as represented by the United States National Aeronautics and Space Administration, Washington, D.C.

[21] Appl. No.: 755,310

[22] Filed: Dec. 29, 1976

[51] Int. Cl.² ................ G01N 25/00; G01N 27/62
[52] U.S. Cl. ................ 23/232 E; 23/232 R; 23/230 PC; 73/23
[58] Field of Search ........... 23/232 R, 232 E, 230 PC

[56] References Cited

U.S. PATENT DOCUMENTS

| | | | |
|---|---|---|---|
| 3,528,779 | 9/1970 | Fontijn | 23/232 E |
| 3,659,100 | 4/1972 | Anderson et al. | 23/232 R UX |
| 3,838,972 | 10/1974 | Richards | 23/232 E X |
| 3,877,819 | 4/1975 | Haas | 23/230 PC |
| 3,923,462 | 12/1975 | Cavanagh | 23/232 R |
| 3,977,831 | 8/1976 | Fletcher et al. | 23/232 R X |

OTHER PUBLICATIONS

Ozone-Induced Chemiluminescence of Organic Compounds, Science, vol. 154, pp. 1454-1459; 1966.

Primary Examiner—Barry S. Richman
Assistant Examiner—Michael S. Marcus
Attorney, Agent, or Firm—John O. Tresansky; Ronald F. Sandler; John R. Manning

[57] ABSTRACT

A method for detecting and measuring trace amounts of aerosols when reacted with ozone in a gaseous environment wherein a sample aerosol is exposed to a fixed ozone concentration for a fixed period of time, a fluorescer added to the exposed sample and thereafter the sample heated in a 30° C/minute linear temperature profile to 200° C. undergoes thermoluminescence the trace peak thereof is measured and recorded as a function of the test aerosol and wherein the recorded thermoluminescence trace peak of the fluorescer is specific to the aerosol being tested.

7 Claims, 2 Drawing Figures

THERMOLUMINESCENT AEROSOL ANALYSIS

ORIGIN OF THE DISCLOSURE

The invention described herein was made by employees of the United States Government and may be manufactured and used by or for the Government for governmental purposes without the payment of any royalties thereon or therefor.

BACKGROUND OF THE INVENTION

The present invention relates to a method for detecting and measuring trace amounts of various aerosols in a gaseous environment. As used herein the term aerosol relates to the organic and inorganic pollutant materials, usually solids, that are suspended within the earth's atmosphere. In one aspect, the invention relates to a method for detecting and measuring specific aerosols which could aid in the development of a detector for rapid identification of effluent sources. Also, the invention could serve as an experimental tool for study of heterogeneous chemistry and study of formation of toxic, electronically excited species in airborne particles.

There are many known methods of determining the presence of trace impurities or various pollutants in a gas such as the earth's atmosphere. However, several of these methods require the use of devices that are cumbersome, expensive, or both, and there is a need for a simple and inexpensive reliable technique. This need is particularly acute in spacecraft and other installations where weight and bulkiness are of primary importance. Previous methods for aerosol analysis include gas and liquid chromatography, mass spectroscopy, electron microscopy, x-ray fluorescence, and wet chemical analysis. Methods for measuring aerosol concentration include high volume samples, turbidity meters, and other particle counting instruments, none of which measure chemical composition.

A previous process for measuring trace amounts of ozone, nitrogen oxide and carbon monoxide, and similar in some respects to the present invention is disclosed in U.S. Pat. No. 3,977,831. This patented process involved pollution detection wherein the pollutant reacted with a solid organic material that inherently chemiluminescensed when heated and the total integrated light intensity, measured during the heated cycle being a measure of pollutant exposure. In the present invention an aerosol is reacted with an ozone environment and the reactant product exposed to a fluorescer. The sample is then subjected to a heating profile, linearly programmed at 30° C. per minute to a temperature of 200° C. The peak intensity of the fluorescer thermoluminescence during this heating serves as an indication of the aerosol tested.

Accordingly, it is an object of the present invention to provide a simple and reliable technique for detecting and measuring trace amounts of various aerosols in a gas. It is further an object to provide such a process which utilizes organic materials that undergo chemical changes and serve as transfer agents or indicators of selected aerosol/ozone reactions and thereafter undergo chemiluminescence when heated.

Another object of the present invention is to provide a process of measuring peak intensity of a thermoluminescent reaction as a function of a specific aerosol.

BRIEF SUMMARY OF THE INVENTION

According to the present invention the foregoing and other objects are attainable by exposing a measured sample of a known aerosol to an ozone gaseous environment, adding a fluorescer to the exposed sample and heating the combined materials at a linear rate of 30° C/minute to a temperature of 200° C. The peak light intensity measured during the heating cycle is a measure of the specific aerosol being tested.

The organic material suitable for detecting trace quantities of aerosols according to the present invention is selected from the group consisting of rubrene, napthacene, poly(ethylene 2, 6-naphtahalene dicarboxylate), 9, 10 dibromo anthracene and 9, 10 diphenyl anthracene. These materials are available as dry solids and are dissolved in a suitable solvent for use in the present invention and must have the inherent chemical property characteristics of being excited by energy transfer from the ozonide in the aerosol.

DETAILED DESCRIPTION

A more complete appreciation of the invention and many of the inherent advantages thereof will be more clearly understood by reference to the following detailed description when considered in connection with the specific examples and accompanying drawings wherein:

FIG. 1 is a schematic diagram of an aparatus useful for measuring the peak thermoluminescent intensity from the aerosol/ozone reaction according to the present invention, and FIG. 2 illustrates the recorder trace from a specific aerosol measured according to the present invention.

Referring now to the drawings and more particularly to FIG. 1, there is shown the apparatus generally designed by reference numeral 10 for detecting and measring peak thermoluminescence according to the present invention. Apparatus 10 includes a housing 12 containing a conventional photomultiplier tube 14 having yellow response and in electrical connection with a suitable power supply 16. A sample container 18 that houses the aerosol that is to be measured for thermoluminescence is positioned in sample holder 20 adjacent programmed heater element 21. Electric leads 22, 23 connect heater element 21 with a suitable power supply and controls, not shown, that increases the heater output to insure a sample increase of 30° C. per minute up to a temperature of 200° C. A thermocouple 24 is in electrical connection with one of the pens on dual pen strip recorder 26 via lead wire 28. The other pen of recorder 26 is in electrical connection with an electrometer 30 via lead 31 to record the output received through lead 32 from photomultiplier 14.

Housing 12 is provided with a pair of openings in the sidewall thereof as designated by reference numerals 34 and 36 shown closed, respectively, by covers 35 and 37. The various components of apparatus 10 are conventional, commercially available items, for example, photomultiplier 14 may be an RCA 7265 photomultiplier; electrometer 30 an Elcor (Model A309B) electrometer available from Elcor, Inc., Falls Church, Virginia, and dual pen recorder 26 is an Electronik 194 from Honeywell, Inc., Fort Washington, Pa. 19034. Thermocouple 24 is a conventional chromel/alumel thermocouple soldered or otherwise thermally connected to sample holder 20 and electrically monitored by recorder 26 to continuously record the temperature of sample 18 as heated. The temperature of heater element 21 was controlled by F&M Scientific Corporation, Model 240M temperature programmer (not shown). When testing for aerosol/ozone reactions according to the present invention, the aerosol sample employed is in solid form. Samples of these aerosols may be collected on sterile filters or like surfaces that are not reactive to the ozone in the environment. An example surface suitable for collection of these samples is a glass surface that has been bleached out relative to ozone reaction.

The operation of the device described above is now believed apparent. In one application of the invention, the sample container 18 housing 2 mg of the sample to be tested for thermoluminescence is placed in sample holder 20 through one of the openings 34, 36. A mixture of 1% ozone in oxygen is then pumped into evacuated housing 12 to provide the gaseous environment therein and the container covers 35 and 37 replaced to close the container.

In this test the samples were exposed to the ozone and oxygen environment for approximately five minutes and covers 35 and 37 then removed to permit ambient air to enter housing 12. After 5—10 minutes, allowed for excess ozone to dissipate, a drop of saturated solution of rubrene in benzene was added to the sample in container 18. The benzene evaporates rapidly, usually 2-5 minutes, and the remaining rubrene is dispersed throughout the aerosol/ozone solid and serves as the fluorescent material which luminesced when excited by the thermal decomposition of the ozonides. This sample is then heated by programmed heater element 21 at a linear rate of 30°/min to a temperature of 200° C. The light emitted by thermoluminescence, is detected by photomultiplier 14, amplified by electrometer 30 and recorded simultaneously with the temperature on dual pen recorder 26.

Figure 2:
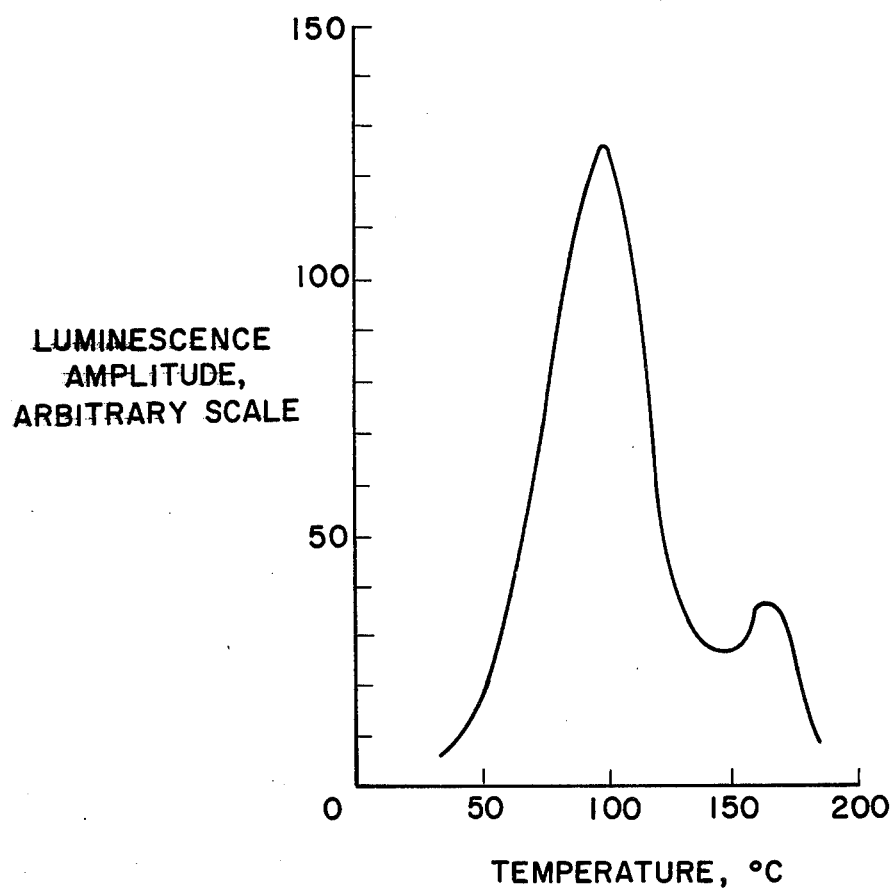

The light output from the sample rises to a maximum as shown in the graph of FIG. 2 for a sample of 1,2 benzanthracene and then decays to zero as the temperature approaches 200° C.

The peak light intensity measured during the heating cycle is a measure of the aerosol being tested. Thus, the luminescent curve obtained has a line shape and maximum that is characteristic to the specific aerosol tested. The parameters listed in the Table below were measured from the recorded output for each of the substances tested.

TABLE

| OZONE/AEROSOL THERMOLUMINESCENCE | | | |
|---|---|---|---|
| Substance | Initial Maximum | Initial Halfwidth | Maximum Four Hr After Ozonation |
| 1293 Aerosol | 97° C. | 81° C. | 100,122,151° C. |
| Rogo Aerosol | 83 | 64 | 102 |
| Ammonium Sulfate | 110 | 44 | — |
| Sodium Chloride | 152 | 52 | — |
| 3,4 Benzpyrene | 103 | 69 | — |
| 1,2 Benzanthracene | 99 | 35 | — |
| Coronene | 85 | 72 | 101 |
| N-Octacosane | 122 | 96 | 130 |
| $Al_2O_3$ | No reaction | | |

A comparison of the parameters in the Table indicates that the various substances are distinguishable on the basis of this simple analysis of the glow curves. The temperature maxima or peak intensity and the linewidths at half maximum are all different. The organic compounds in the Table are known constituents of urban aerosols. The cosanes constitute 85% of the organics in urban aerosols. Ammonium sulfate is a primary sulfate in the atmosphere and a product of $SO_2$ oxidation. NaCl is an aerosl in the coastal regions. Aluminum oxide did not display a reaction with ozone. A more detailed analysis of line shapes should reveal other characteristics that are unique to the substance tested. Only the line shape for 1,2, benzanthracene (FIG. 2) is included in the present application in the interest of clarity. The other line shapes are similar but with the noted different initial maximum and initial half width maximums.

The aerosols identified as "1293 aerosol" and "ROGO aerosol" were collected at two different sites as precipitated particles from the local atmosphere and are mixtures of many compounds. The site selection for these two aerosols were not sterilized or in any manner prepared for the sample collection. The glow curves obtained from these aerosols are reproducible and therefore could be compared with aerosls from known pollution sources to identify the source. Such comparison would be an invaluable aid for tracing dispersion of pollutants as well as determining the identity of the source.

The thermoluminescence curves may also be useful in qualitative analysis of the aerosol composition. This is accomplished by comparison of the aerosol luminescence curves with curves obtained from a mixture of chemical species that are known constituents of aerosol. For a specific geographical area there would be a limited number of species. A catalog of glow curves could be produced by measuring aerosols from various sources and analyzing their chemical compostion by standard methods. Identification of the aerosol would then be accomplished by simply comparing the flow curves obtained in the field to the cataloged curves. Also this catalog of curves could be stored in a computer and during printout of the "unknown" trace the corresponding curve peaks could be compared and the "unknown" readily identified.

Four of the samples in the Table above were examined four hours after ozonation and found to reproduce a glow curve different from those found immediately after ozonation. In the case of "1293 Aerosol", several peaks were exhibited. Since the ozonides formed initially are unstable, new chemical species are formed at various rates and glow curves such as these provide additional data for characterizing and identifying the aersol constituents.

The above detailed description of specific tests is exemplary of the present invention and are by no means considered exhaustive. These experiments were all ozonated in the laboratory at 1% ozone concentration. Interactions of $(NH_4) HSO_4$ with ozone at ozone concentrations of one part per million (ppm) have also been note. Trace amounts of ozone of this concentration are present on the earth's atmosphere at all levels and it can therefore be assumed that airborne aerosols are ozonated naturally, although not to the extent produced under the controlled laboratory tests as shown in the Table. However, with more sensitive photon detection devices, the ozonides produced naturally could be detected using procedures analogous to these described herein and the need for laboratory ozonation would be eliminated.

The temperature at which the peak intensity in the flow curve occurs is representative of the stability of the ozonides formed and can be related to activation energy for the thermal decomposition thereof. For a reaction following first order kinetics, the position of the peak depends only on the type of compounds formed and time after ozonation, and not in the concentration of these compounds in the mixture. Under such conditions the peak in the glow curve will not depend on the amount of ozone that has reacted with the aerosol and is therefore specific to the aerosol.

It is thus seen that the present invention provides a process for readily determining the presence and identity of various aerosols in the test sample and can serve as an aid in determining the source of such aersols in a specific geographic area. This is accomplished by the heterogeneous interaction occuring between the known various organic and inorganic atmosphere aerosols and ozone. This interaction is observable in the laboratory by utilizing a fluorescer as a transfer agent or indicator for the aerosol/ozone interaction and by using a thermoluminescence technique to obtain a luminescent spectrum. This spectrum is different for each compound and is thus characteristic of the molecular structure of the compound. This spectra also changes with time after ozonation and thus additional chemical reactions take place after the initial heterogeneous complexing. With available meterological data at the test site, these properties make the present invention of a sensitive thermoluminescent process applicable for detecting and tracking aerosols to their source, i.e., smoke stacks, chemical plants, steel mills, etc. Additionally, the instrumentation requirements for the present invention make the process readily suitable for source identification in the field as well as for ground truth and flight experiments.

Also, the present invention provides a useful tool for parameter evaluation in atmospheric chemistry models which include aerosols and in the basic study of heterogeneous chemistry. The observations of luminescence indicate that the aerosol/ozone complex is a high energy species with serious implications with respect to toxic biological properties such as mutagenicity and carcinogenicity. Another unique advantage of the present invention is the sensitivity of the process. Solid reaction rates as low as $10^{-9}$ mole/year and liquid reaction rates as low as $10^{-14}$ mole/year can be measured by the process described herein.

Although the invention has been described relative to use of precise equipment and with specific illustrative examples, it is not so limited. There are obviously many modifications and variations of the present invention that will be readily apparent to those skilled in the art in the light of the above teachings. It is therefore to be understood that the invention may be practiced otherwise than as specifically described herein within the scope of the appended claims.

What is claimed as new and desired to be secured by Letters Patent of the United States is:

1. A method for detecting and identifying trace amounts of aerosols in an atmospheric environment comprising:

collecting a sample of the aerosol to be tested;

exposing the collected sample to a controlled gaseous environment having a known quantity of ozone therein, for a fixed period of time, to thereby facilitate an aerosol/ozone reaction;

adding a fluorescer indicator to the reacted sample;

heating the combined sample at a linear programmed rate of 30° C/min to a temperature of 200° C.;

detecting the thermoluminescence of the fluorescer during the heating cycle, and recording a trace of the thermoluminescent output during the heating cycle with the peak output thereof being indicative of the specific aerosol.

2. The method of claim 1 wherein the aerosol tested includes a mixture of pollutants and the recorded trace includes specific peaks at specific temperatures in the heating cycle that are indicative of each individual pollutant.

3. The method of claim 1 wherein the fluorescer is selected from the group consisting of rubrene, napthacene, 9,10 diphenyl anthracene and 9,10 dibromo anthracene.

4. The method of claim 1 including the step of comparing the recorded trace peak with known or suspected aerosol sources in a specific geographic area to aid in identifying the pollutant source.

5. The method of claim 1 wherein 2 mg of the collected sample is exposed to a controlled gaseous environment consisting of 1% ozone in oxygen for a period of five minutes.

6. The method of claim 1 wherein the fluorescer is dissolved in a solvent and added to the aerosol/ozone reaction product as a liquid.

7. The method of claim 6 wherein the solvent is benezene.

* * * * *